United States Patent [19]
Chalfie et al.

[11] Patent Number: 6,146,826
[45] Date of Patent: *Nov. 14, 2000

[54] GREEN FLUORESCENT PROTEIN

[75] Inventors: Martin Chalfie, New York, N.Y.; Douglas Prasher, East Falmouth, Mass.

[73] Assignees: The Trustees of Columbia University in the City of New York, New York, N.Y.; Woods Hole Oceanographic Institution, Woods Hole, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/367,236

[22] PCT Filed: Sep. 9, 1994

[86] PCT No.: PCT/US94/10165

§ 371 Date: Jun. 18, 1996

§ 102(e) Date: Jun. 18, 1996

[87] PCT Pub. No.: WO95/07463

PCT Pub. Date: Mar. 16, 1995

Related U.S. Application Data

[63] Continuation-in-part of application No. 08/192,274, Feb. 4, 1994, abandoned, which is a continuation-in-part of application No. 08/119,678, Sep. 10, 1993, Pat. No. 5,491,084.

[51] Int. Cl.$^7$ .............................. C12Q 1/68; C12N 1/15; C12N 1/21; C12N 5/10
[52] U.S. Cl. .................... 435/6; 435/69.1; 435/252.3; 435/254.11; 435/254.2; 435/325; 435/419; 435/455; 435/471
[58] Field of Search .............................. 435/6, 69.1, 69.7, 435/69.8, 189, 240.2, 240.4, 172.3, 320.1, 253, 325, 419, 455, 471, 252.3, 254.11, 254.2; 530/350; 536/23.1, 23.2, 23.4, 23.5, 24.1

[56] References Cited

U.S. PATENT DOCUMENTS

| | | | |
|---|---|---|---|
| 5,268,463 | 12/1993 | Jefferson | 536/23.7 |
| 5,491,084 | 2/1996 | Chalfie et al. | 435/189 |

FOREIGN PATENT DOCUMENTS

| | | |
|---|---|---|
| 0540064 | 5/1993 | European Pat. Off. . |
| WO9101305 | 2/1991 | WIPO . |
| WO9417208 | 8/1994 | WIPO . |
| WO9423039 | 10/1994 | WIPO . |

OTHER PUBLICATIONS

Cubitt, A.B. et al, (1995) "Understanding, improving and using green fluorescent proteins," *TIBS Trends in BiochemicalSciences*, 20:448–455.

Inouye, S. And Tsuji, F.I., (1994) "Aequorea green fluorescent protein –Expression of the gene and fluorescence characteristics of the recombinant protein," *FEBS Letters* 341:277–280.

Perozzo, et al., (1987), "X–ray Diffraction and Time–resolved Fluorescence Analyses of Aequorea Green Fluorescent Protein Crystals" *The Journal of Biological Chemistry* 7713–7716.

Prasher, D.C., (1995) "Using GFP to see the light" *Science* 11:320–323.

Prendergast, F.G. and Mann, K.G., (1978) "Chemical and physical properties of Aequorin and the green fluorescent protein isolated from Aequorea forskalea," *Biochemistry* 17:3448–3453.

Ward, W.W. and Bokman, S.H., (1982) "Reversible denaturation of Aequorea green–fluorescent protein: Physical separation and characterization of the renatured protein," *Biochemistry* 21:4535–4544.

"Glowing method is found to tag work of genes," (1994) Columbia University Record, 19:1 and 6.

Chalfie, M. et al. (1994) "Green Fluorescent Protein as a Marker for Gene Expression" Science, vol. 263: 802–805.

Fire, A. et al. (1990) "A modular set of lacZ fusion vectors for studying gene expression in *Caenorhabditis elegans*", Gene, vol. 93: 189–198.

Morise, H. et al. (1974) "Intermolecular Energy Transfer in the Bioluminescent System of Aequorea" Biochemistry, vol. 13, No. 12: 2656–2662.

Shimomura, O. (1979) "Structure of the Chromophore of Aequorea Green Fluorescent Protein", FEBS Letters, vol. 104, No. 2: 220–222.

Webster's II New Riverside University Dictionary, (1994) Soukhanov et al. eds. p. 775.

*Primary Examiner*—Robert A. Schwartzman
*Attorney, Agent, or Firm*—John P. White; Cooper & Dunham LLP

[57] ABSTRACT

This invention provides a cell comprising a DNA molecule having a regulatory element from a gene, other than a gene encoding a green fluorescent protein operatively linked to a DNA sequence encoding the green fluorescent protein. This invention also provides living organisms which comprise the above-described cell. This invention also provides a method for selecting cells expressing a protein of interest which comprises: a) introducing into the cells a DNAI molecule having DNA sequence encoding the protein of interest and DNAII molecule having DNA sequence encoding a green fluorescent protein; b) culturing the introduced cells under conditions permitting expression of the green fluorescent protein and the protein of interest; and c) selecting the cultured cells which express green fluorescent protein, thereby selecting cells expressing the protein of interest. Finally, this invention provides various uses of a green fluorescent protein.

26 Claims, 3 Drawing Sheets

# GREEN FLUORESCENT PROTEIN

This application is a continuation-in-part of U.S. Ser. Nos. 08/119,678, U.S. Pat. No. 5,491,084, and 08/192,274, abandoned, International Applicaton No. PCT/US94/10165 filed Sept. 10, 1993 and Feb. 4, 1994, Sep. 9, 1994 respectively, the contents of which are hereby incorporated by reference.

The invention disclosed herein was made with Government support under NIH Grant No. 5R01GM30997 from the Department of Health and Human Services. Accordingly, the U.S. Government has certain rights in this invention.

BACKGROUND OF THE INVENTION

Throughout this application various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

Several methods are available to monitor gene activity and protein distribution within cells. These include the formation of fusion proteins with coding sequences for β-galactosidase (22), and luciferases (22). The usefulness of these methods is often limited by the requirement to fix cell preparations or to add exogenous substrates or cofactors. This invention disclose a method of examining gene expression and protein localization in living cells that requires no exogenously-added compounds.

This method uses a cDNA encoding the Green fluorescent Protein (GFP) from the jelly fish *Aequorea victoria* (3). In *A. victoria*, GFP absorbs energy generated by aequorin upon the stimulation by calcium and emits a green light.

This invention discloses that GFP expressed in prokaryotic and eukaryotic cells is capable of producing a strong green fluorescence when excited with near UV or blue light. Since this fluorescence requires no additional gene products from *A. victoria*, chromophore formation is not species specific.

SUMMARY OF THE INVENTION

This invention provides a cell comprising a DNA molecule having a regulatory element from a gene, other than a gene encoding a green fluorescent protein operatively linked to a DNA sequence encoding the green fluorescent protein. This invention also provides living organisms comprising the above-described cell.

This invention provides a method for selecting cells expressing a protein of interest which comprises: a) introducing into the cells a DNAI molecule having DNA sequence encoding the protein of interest and DNAII molecule having DNA sequence encoding a green fluorescent protein; b) culturing the introduced cells in conditions permitting expression of the green fluorescent protein and the protein of interest; and c) selecting the cultured cells which express green fluorescent protein, thereby selecting cells expressing the protein of interest.

This invention also provides a method for localizing a protein of interest in a cell: a) introducing into a cell a DNA molecule having DNA sequence encoding the protein of interest linked to DNA sequence encoding the green fluorescent protein such that the protein produced by the DNA molecule will have the protein of interest fused to the green fluorescent protein; b) culturing the cell in conditions permitting expression of the fused protein; c) detecting the location of the fused protein product, thereby localizing the protein of interest.

DETAILED DESCRIPTION OF THE INVENTION

Figure 1:
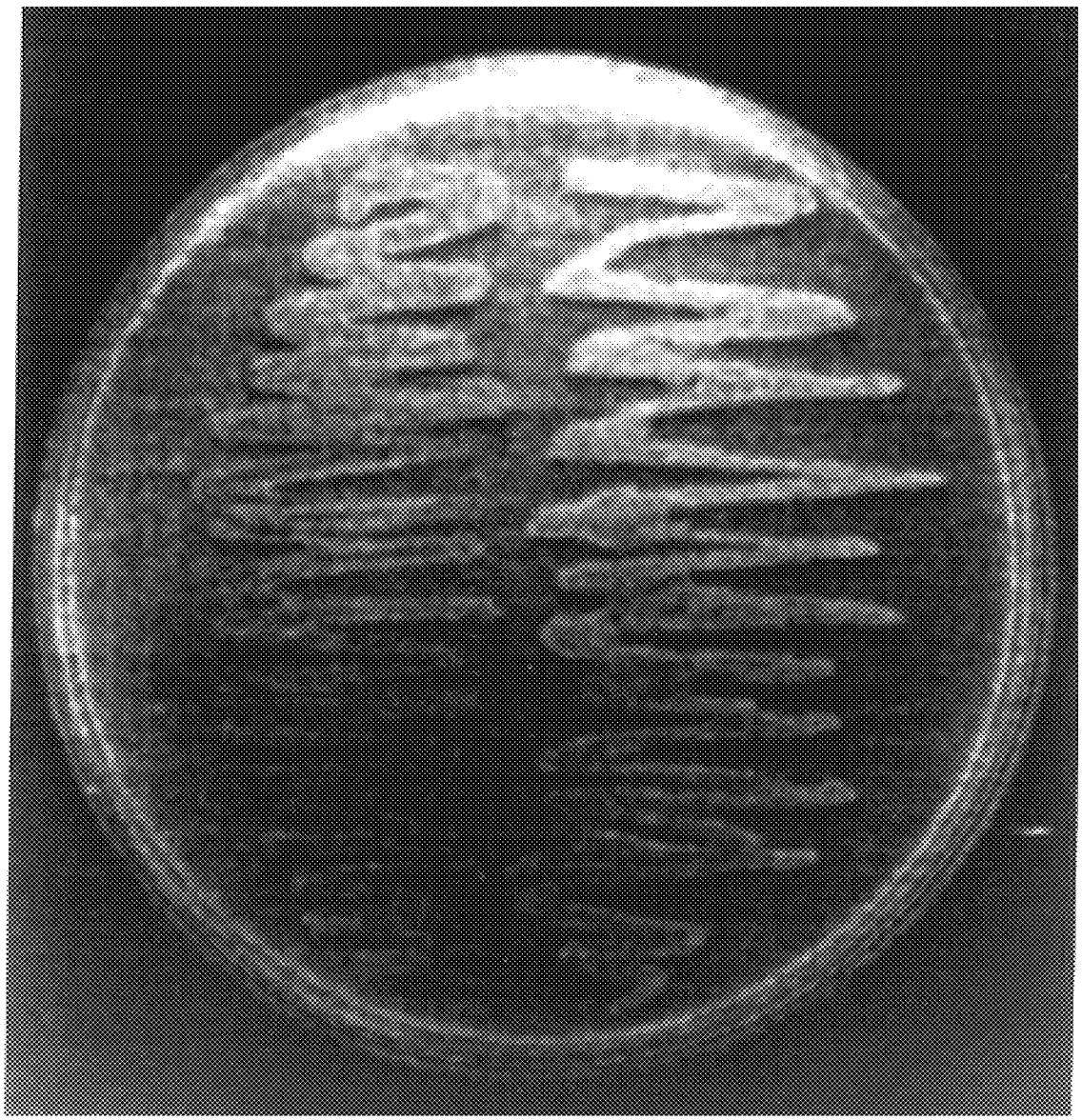
FIG. 1 Expression of GFP in *E. coli*. The bacteria on the right side of the figure have the GFP expression plasmid. This photograph was taken while irradiating the agar plate with a hand-held long-wave UV source.

Throughout this application, the following standard abbreviations are used to indicate specific nucleotides:

| C = cytosine | A = adenosine |
|---|---|
| T = thymidine | G = guanosine |

This invention provides a cell comprising a DNA molecule having a regulatory element from a gene, other than a gene encoding a green fluorescent protein operatively linked to a DNA sequence encoding the green fluorescent protein.

This invention provides a cell comprising a DNA molecule having a regulatory element from a gene, other than a gene encoding a green fluorescent protein operatively linked to a DNA sequence encoding the green fluorescent protein, wherein the cell is selected from a group consisting essentially of bacterial cell, yeast cell, fungal cell, insect cell, nematode cell, plant or animal cell.

Suitable animal cells include, but are not limited to Vero cells, HeLa cells, Cos cells, CVI cells and various vertebral, invertebral, mammalian cells.

In an embodiment, the bacterial cell is Escherichia coli. As used herein, "a regulatory element" from a gene is the DNA sequence which is necessary for the transcription of the gene.

In this invention, the term "operatively linked" means that following such a link the regulatory element can direct the transcription of the linked protein-coding DNA sequence.

The gene encoding a green fluorescent protein includes DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms.

These DNA molecules include: the incorporation of codons "preferred" for expression by selected mammalian or non-mammalian hosts; the provision of sites for cleavage by restriction endonuclease enzymes; and the provision of additional initial, terminal or intermediate DNA sequences that facilitate construction of expression vectors.

As an example, plasmid pGFP10.1 codes for a mutated GFP protein having the 80th amino acid residue as an arginine rather than a glutamine predicted to be in native GFP from *A. Victoria*. This mutated protein retains the property to fluoresce like the natural protein.

In an embodiment, the regulatory element is a promoter. In a further embodiment, the promoter is activated by a heavy metal. Such promoters are well-known in the art (J. H. Freedman, L. W. Slice, A. Fire, and C. S. Rubin (1993) Journal of *Biological Chemistry*, 268:2554).

In another embodiment, the promoter is that from a cytochrome P450 gene. Cytochrome P450 is well-known in the art and there are a number of P450 promoters known.

In still another embodiment, the promoter is that from a stress protein gene. Such stress proteins are well-known in the art (E. G. Stringham, D. K. Dixon, D. Jones and E. D. Candido (1992) *Molecular Biology of the Cell*, 3:221; and William J. Welch (May, 1993), Scientific American, page 56). In a further embodiment, the stress protein is a heat-shock protein.

This invention provides a cell comprising a DNA molecule having a regulatory element from a gene, other than a gene encoding a green fluorescent protein operatively linked to a DNA sequence encoding the green fluorescent protein, wherein the promoter is from a gene necessary for the viability of a cell.

In another embodiment, the regulatory element is an enhancer. Enhancers are well-known in the art.

This invention provides a cell comprising a DNA molecule having a regulatory element from a gene, other than a gene encoding a green fluorescent protein operatively linked to a DNA sequence encoding the green fluorescent protein, wherein the DNA sequence encodes the Aequorea victoria green fluorescent protein.

In an embodiment, the Aequorea victoria green fluorescent protein is cloned in a plasmid. This plasmid is a modification of the pBS(+) (formerly called Bluescribe+) vector (Stratagene®) which has inserted within it an EcoRI fragment containing the cDNA sequence of the Aequorea Victoria green fluorescent protein (as modified herein). The fragment was obtained from λFP10 (Prasher, D. C., Eckenrode, V. K., Ward, W. W.; Prendergast, F. G., and Cormier, M. J., (1992) Primary structure of the *Aequorea victoria* green fluorescent protein. *Gene*, 111:229–233) by amplification using the polymerase chain reaction (Saiki, R. K., Gelfand, D. H., Stoffel, S., Sharf, S. J., Higuchi, G. T., Horn, G. T., Mullis, K. B., and Erlich, H. A. (1988) Primer-directed enzymatic amplification of DNA with a thermostable DNA polymerase. *Science*, 239:487–491) with primers flanking the EcoRI sites and subsequent digestion with EcoRI. The sequence of the cDNA in pGFP10.1 differs from the published sequence (5) by a change of the 80th codon of the coding sequence from CAG to CGG, a change that replaces a glutamine with arginine in the protein sequence.

This pGFP10.1 plasmid was deposited on Sep. 1, 1993 with the American Type Culture Collection (ATCC), 10801 University Boulevard, Manassas, Va. 20110, U.S.A. under the provisions of the Budapest Treaty for the International Recognition of the Deposit of Microorganism for the Purposes of Patent Procedure. Plasmid pGFP10.1 was accorded ATCC Accession Number 75547.

In another embodiment, this invention provide a bacterial cell which is expressing the green fluorescent protein. In an further embodiment, the bacterial cell is an *E. coli* cell. In a still further embodiment, this *E. coli* cell is designated SMC1 (ATCC Accession No. 69554).

This SMC1 bacterial cell was deposited on Feb. 4, 1994, 1993 with the American Type Culture Collection (ATCC), 10801 University Boulevard, Manassas, Va. 20110, U.S.A. under the provisions of the Budapest Treaty for the International Recognition of the Deposit of Microorganism for the Purposes of Patent Procedure. Bacterial cell SMC1 was accorded ATCC Accession Number 69554.

This invention further provides an isolated green fluorescent protein produced from the above-described cells which comprise a DNA molecule having a regulatory element from a gene, other than a gene encoding a green fluorescent protein operatively linked to a DNA sequence encoding the green fluorescent protein. This isolated green fluorescent protein can then be further modified in vitro for various uses.

This invention disclose an efficient method for expression of green fluorescent protein such that large amount of the protein could be produced. Methods to isolate expressed protein have been well-known and therefore, green fluorescent protein may be isolated easily.

This invention provides a living organism comprising the cell comprising a DNA molecule having a regulatory element from a gene, other than a gene encoding a green fluorescent protein operatively linked to a DNA sequence encoding the green fluorescent protein.

In another embodiment, the living organism is human. In another embodiment, the living organism is a mouse. The living organism may be other mammals. In addition, this invention is applicable to other vertebrates, non-vertebrates and living organisms.

In an embodiment, the living organism is *C. elegans*. In still another embodiment, the living organism is Drosophila, zebra fish, virus or bacteriophage.

A bacteriophage carrying the green fluorescent protein gene can infect a particular type of bacteria. The infection may be easily detected via the expression of the green fluorescent protein. Therefore, by using appropriate bacteriophages, the presence of that particular type of bacteria may be detected.

Similarly, a eucaryotic virus carrying the green fluorescent protein gene may infect a specific cell type. The infection may be easily detected by monitoring the expression of the green fluorescent protein.

Methods to introduce exogenous genetic material into a cell are well-known in the art. For example, exogenous DNA material may be introduced into the cell by calcium phosphate precipitation technology. Other technologies, such as the retroviral vector technology, electroporation, lipofection and other viral vector systems such as adeno-associated virus system, or microinjection may be used.

The above-described cells and living organisms are useful to detect effects of external stimulus to the regulatory element. The stimulus may have direct or indirect effects on the regulatory element. Such effects will be detectable through either the induction of expression and production of the green fluorescent protein or switching off the expression of the green fluorescent protein.

Cells expressing the green fluorescent proteins may be conveniently separated by a fluorescence-activated cell sorter.

These cells and organisms may be used to detect the presence of different molecules in various kinds of biological samples such as blood, urine or saliva. By operatively linking a regulatory element of the gene which is affected by the molecule of interest to a green fluorescent protein, the presence of the molecules will affect the regulatory element which in turn will affect the expression of the green fluorescent protein. Therefore, the above-described cells are useful for the detection of molecules. Such detection may be used for diagnostic purposes. An example of such a molecule is a hormone.

This invention provides a living organism comprising the cell comprising a DNA molecule having a regulatory element from a gene, other than a gene encoding a green fluorescent protein operatively linked to a DNA sequence encoding the green fluorescent protein, wherein the regulatory element is for a stress protein.

This invention provides a living organism comprising the cell comprising a DNA molecule having a regulatory element from a gene, other than a gene encoding a green fluorescent protein operatively linked to a DNA sequence encoding the green fluorescent protein, wherein the stress protein is a heat-shock protein.

This invention provides a method to produce green fluorescent protein comprising a) culturing the above-described cells comprising a DNA molecule having a regulatory element from a gene, other than a gene encoding a green fluorescent protein operatively linked to a DNA sequence encoding the green fluorescent protein; and b) isolating and purifying the green fluorescent protein produced from the cells. Standard methods for isolating and purifying proteins are well-known in the art. In an embodiment, the cells used for production of green fluorescent proteins are E. coli cells. In a further embodiment, the E. coli cells are cultured aerobically.

This invention provides a method to synthesize green fluorescent protein comprising a) culturing the cell designated SMC1; and b) isolating and purifying the green fluorescent protein produced from the cell.

This invention provides a method for selecting cells expressing a protein of interest which comprises: a) introducing into the cells a DNAI molecule having DNA sequence encoding the protein of interest and DNAII molecule having DNA sequence encoding a green fluorescent protein; b) culturing the introduced cells in conditions permitting expression of the green fluorescent protein and the protein of interest; and c) selecting the cultured cells which express green fluorescent protein, thereby selecting cells expressing the protein of interest.

This invention also provides the above method, wherein the cells are selected from a group consisting essentially of bacterial cells, yeast cells, fungal cells, insect cells, nematode cells, plant or animal cells. Suitable animal cells include, but are not limited to Vero cells, HeLa cells, Cos cells, CV1 cells and various primary mammalian cells.

In an embodiment, DNAI and DNAII are linked. In another embodiment, the DNA encodes the Aequorea Victoria green fluorescent protein.

This invention provides a method for localizing a protein of interest in a cell which comprises: a) introducing into a cell a DNA molecule having DNA sequence encoding the protein of interest linked to DNA sequence encoding a green fluorescent protein such that the protein produced by the DNA molecule will have the protein of interest fused to the green fluorescent protein; b) culturing the cell in conditions permitting expression of the fused protein; and c) detecting the fused protein composed of the green fluorescent protein in the cell, thereby localizing a protein of interest in a cell.

Regulatory elements required for expression include promoter sequences to bind RNA polymerase and translation initiation sequences for ribosome binding. For example, a bacterial expression vector includes a promoter such as the lac promoter and for translation initiation the Shine-Dalgarno sequence and the start codon ATG. Similarly, a eukaryotic expression vector includes a heterologous or homologous promoter for RNA polymerase II, a downstream polyadenylation signal, the start codon ATG, and a termination codon for detachment of the ribosome. Such vectors may be obtained commercially or assembled from the sequences described by methods well-known in the art, for example the methods described above for constructing vectors in general.

To maximize the expression of the green fluorescent protein, the sequence flanking the translation initiation codon may be modified (reviewed by Kozak, 1984), compilation and analysis of sequences upstream from the translation start site in eucaryotic mRNAs. Nucl. Acids. Res. 12:857–872). A sequence may then be generated to produce higher amounts of the GFP protein.

In addition, artificial introns may be introduced so as to increase the production of the protein.

Other special targeting sequences may be inserted into the GFP gene. One such targeting sequence is the nuclear localization signal (such as the SV40 nuclear localization signal).

The host cell of the above expression system may be selected from the group consisting of the cells where the protein of interest is normally expressed, or foreign cells such as bacterial cells (such as E. coli), yeast cells, fungal cells, insect cells (such as Sf9 cell in the baculovirus expression system), nematode cells, plant or animal cells, where the protein of interest is not normally expressed. Suitable animal cells include, but are not limited to Vero cells, HeLa cells, Cos cells, CV1 cells and various primary mammalian cells.

In an embodiment of the method for localizing a protein of interest in a cell, the DNA encoding the green fluorescent protein is from *Aequorea victoria*.

This invention provides a method for localizing a protein of interest in a cell which comprises: a) introducing into a cell a DNA molecule having DNA sequence encoding the protein of interest linked to DNA sequence encoding a green fluorescent protein such that the protein produced by the DNA molecule will have the protein of interest fused to the green fluorescent protein; b) culturing the cell in conditions permitting expression of the fused protein; and c) detecting the location of the fused protein composed of green fluorescent protein in the cell, thereby localizing a protein of interest in a cell, wherein the cell normally expressing the protein of interest.

This invention provides a method for detecting expression of a gene in a cell which comprises: a) introducing into the cell a DNA molecule having DNA sequence of the gene linked to DNA sequence encoding a green fluorescent protein such that the regulatory element of the gene will control expression of the green fluorescent protein; b) culturing the cell in conditions permitting expression of the gene; and c) detecting the expression of the green fluorescent protein in the cell, thereby indicating the expression of the gene in the cell.

This invention provides a method for indicating expression of a gene in a subject which comprises: a) introducing into a cell of the subject a DNA molecule having DNA sequence of the gene linked to DNA sequence encoding a green fluorescent protein such that the regulatory element of the gene will control expression of the green fluorescent protein; b) culturing the cell in conditions permitting expression of the fused protein; and c) detecting the expression of the green fluorescent protein in the cell, thereby indicating the expression of the gene in the cell.

In an embodiment of the above methods, the green fluorescent protein is the Aequorea victoria green fluorescent protein.

This invention provides a method for determining the tissue-specificity of transcription of a DNA sequence in a subject which comprises: a) introducing into a cell of the subject a DNA molecule having the DNA sequence linked to DNA sequence encoding a green fluorescent protein such that the DNA sequence will control expression of the green fluorescent protein; b) culturing the subject in conditions permitting the expression of the green fluorescent protein; and c) detecting the expression of the green fluorescent protein in different tissue of the subject, thereby determining the tissue-specificity of the expression of the DNA sequence.

This invention provides a method for determining the presence of heavy metal in a solution which comprises: a) culturing the cell comprising a DNA molecule having a promoter from a gene, other than a green fluorescent protein operatively linked to a DNA sequence encoding the green fluorescent protein, wherein transcription at the promoter is activated by a heavy metal in the solution; and b) detecting expression of the green fluorescent protein, the expression of the green fluorescent protein indicates the presence of heavy metal.

This invention provides a method for detecting pollutants in a solution which comprises: a) culturing the cell comprising a DNA molecule having a promoter from a gene, other than a green fluorescent protein operatively linked to a DNA sequence encoding the green fluorescent protein, wherein the promoter is activated by a heavy metal or a toxic organic compound or the promoter is for a stress protein in the solution; and b) detecting expression of the green fluorescent protein, the expression of the green fluorescent protein indicates the presence of pollutants in the solution.

Finally, this invention provides a method for producing fluorescent molecular weight markers comprising: a) linking a DNA molecule encoding a green fluorescent protein with a DNA molecule encoding a known amino acid sequence in the same reading frame; b) introducing the linked DNA molecule of step a) in an expression system permitting the expression of a fluorescent protein encoded by the linked DNA molecule; and c) determining the molecular weight of the expressed fluorescent protein of step b), thereby producing a fluorescent molecular weight marker.

Various expression systems are known in the art. The E. coli expression system, one of the commonly used system is described in the following section.

The determination of molecular weight may be done by comparing the expressed fluorescent protein of step b) with known molecular weight markers. Alternatively, the molecular weight can be predicted by calculation since the linked DNA sequence is known (and so is the amino acid sequence being encoded). In an embodiment, the expressed fluorescent protein is purified. The purified fluorescent protein can be conveniently used as molecular weight markers.

This invention will be better understood from the Experimental Details which follow. However, one skilled in the art will readily appreciate that the specific methods and results discussed are merely illustrative of the invention as described more fully in the claims which follow thereafter.

Experimental Details

A cDNA for the Aequorea victoria green fluorescent protein (GFP) produces a fluorescent product when expressed in prokaryotic (Escherichia coli) or eukaryotic (Caenorhabditis elegans) cells. Because exogenous substrates and cofactors are not required for this fluorescence, GFP expression can be used to monitor gene expression and protein localization in living organisms.

Light is produced by the bioluminescent jellyfish Aequorea victoria when calcium binds to the photoprotein aequorin (1). Although activation of aequorin in vitro or in heterologous cells produces blue light, the jellyfish produces green light. This latter light is the result of a second protein in A. victoria that derives its excitation energy from aequorin (2), the green fluorescent protein (GFP).

Purified GFP, a protein of 238 amino acids (3), absorbs blue light (maximally at 395 nm with a minor peak at 470 nm) and emits green light (peak emission at 509 nm with a shoulder at 540 nm) (2, 4). This fluorescence is very stable; virtually no photobleaching is observed (5). Although the intact protein is needed for fluorescence, the same absorption spectral properties found in the denatured protein are found in a hexapeptide that starts at amino acid 64 (6, 7). The GFP chromophore is derived from the primary amino acid sequence through the cyclization of Ser-dehydroTyr-Gly within this hexapeptide (7). The mechanisms that produce the dehydrotyrosine and cyclize the polypeptide to form the chromophore are unknown. To determine whether additional factors from A. victoria were needed for the production of the fluorescent protein, applicants tested GFP fluorescence in heterologous systems. Here applicants show that UFP expressed in prokaryotic and eukaryotic cells is capable of producing a strong green fluorescence when excited by blue light. Because this fluorescence requires no additional gene products from A. Victoria, chromophore formation is not species specific and occurs either through the use of ubiquitous cellular components or by autocatalysis.

Figure 2:
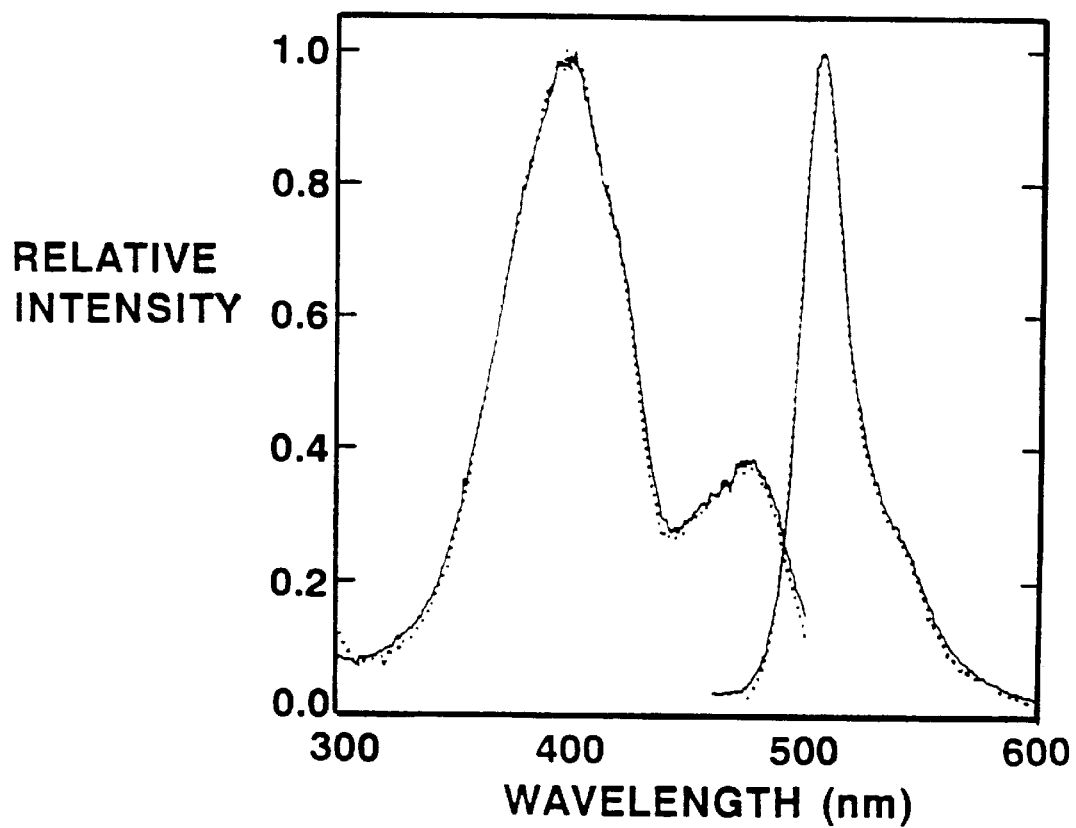
FIG. 2 Excitation and Emission Spectra of *E. coli*-generated GFP (solid lines) and purified *A. victoria* GFP (L form; dotted lines).

Expression of GFP in Escherichia coli (8) under the control of the T7 promoter results in a readily detected green fluorescence (9) that is not observed in control bacteria. Upon illumination with a long-wave UV source, fluorescent bacteria were detected on agar plates containing the inducer isopropyl-β-D-thiogalactoside (IPTG) (FIG. 1). When GFP was partially purified from this strain (10), it was found to have fluorescence excitation and emission spectra indistinguishable from those of the purified native protein (FIG. 2). The spectral properties of the recombinant GFP suggest that the chromophore can form in the absence of other A. victoria products.

Figure 3:
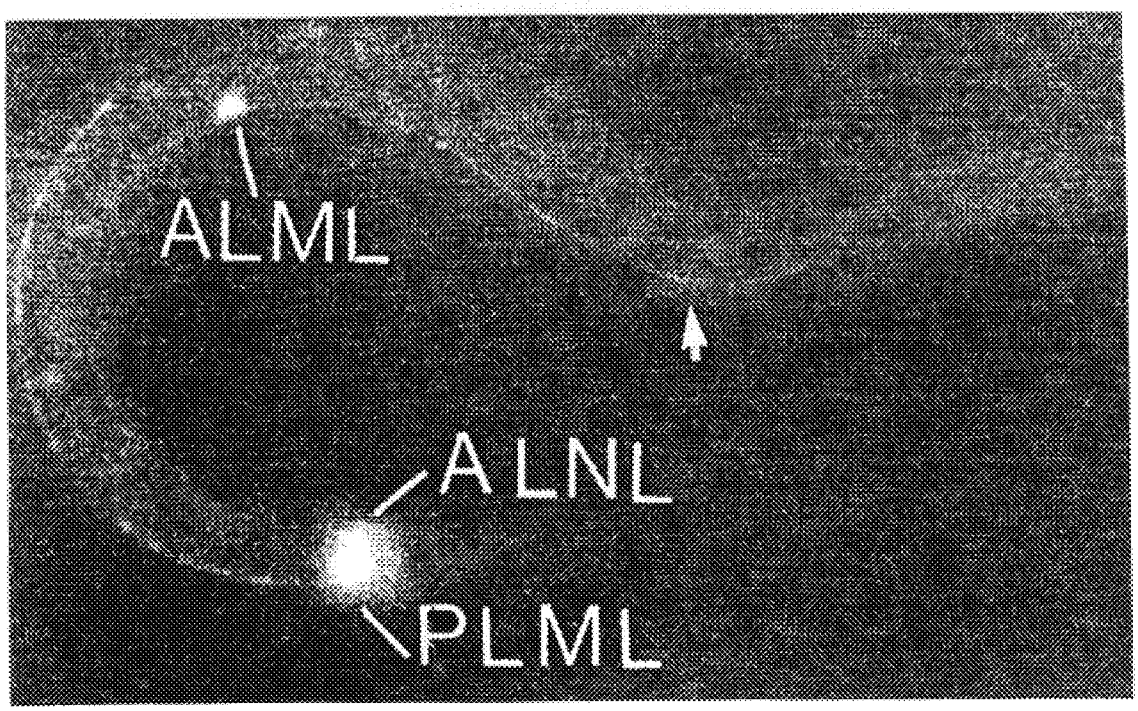
FIG. 3 Expression of GFP in a first stage *Caenorhabditis elegans* larva. Two touch receptor neurons (PLML and ALML) and one other neuron of unknown function (ALNL) are indicated. Processes can be seen projecting from all three cell bodies. The arrow points to the nerve ring branch from the ALML cell (out of focus). The background fluorescence is due to the animal's autofluorescence.

Transformation of the nematode Caenorhabditis elegans also resulted in the production of fluorescent GFP (11) (FIG. 3). GFP was expressed in a small number of neurons under the control of a promoter for the mec-7 gene. The mec-7 aene encodes a β-tubulin (12) that is abundant in six touch receptor neurons in C. elegans and less abundant in a few other neurons (13, 14). The pattern of expression of GFP was similar to that detected by MEC-7 antibody or from mec-7lacZ fusions (13–15). The strongest fluorescence was seen in the cell bodies of the four embryonically-derived touch receptor neurons (ALML, ALMR, PLML, PLMR) in younger larvae. The processes from these cells, including their terminal branches, were often visible in larval animals. In some newly hatched animals, the PLM processes were short and ended in what appeared to be prominent growth cones. In older larvae, the cell bodies of the remaining touch cells (AVM and PVM) were also seen; the processes of these cells were more difficult to detect. These postembryonically-derived cells arise during the first of the four larval stages (16), but their outgrowth occurs in the following larval stages (17), with the cells becoming functional during the fourth larval stage (18). GFP's fluorescence in these cells is consistent with these previous results: no fluorescence was detected in these cells in newly hatched or late first-stage larvae, but it was seen in four of ten late second-stage larvae, all nine early fourth-stage larvae, and seven of eight young adults (19). In addition, moderate to weak fluorescence was seen in a few other neurons (FIG. 3) (20). The details of the expression pattern are being examined.

Like the native protein, GFP expressed in both E. coli and C. elegans is quite stable (lasting at least ten minutes) when illuminated with 450–490 nm light. Some photobleaching occurs, however, when the cells are illuminated with 340–390 nm or 395–440 nm light (21).

Several methods are available to monitor gene activity and protein distribution within cells. These include the formation of fusion proteins with coding sequences for β-galactosidase, firefly luciferase, and bacterial luciferase (22). Because such methods require exogenously-added substrates or cofactors, they are of limited use with living tissue. Because the detection of intracellular GFP requires only irradiation by near UV or blue light, it is not substrate limited. Thus, it should provide an excellent means for monitoring gene expression and protein localization in living cells (23, 24). Because it does not appear to interfere with cell growth and function, GFP should also be a convenient indicator of transformation and one that could allow cells to be separated using fluorescence-activated cell sorting. Applicants also envision that GFP can be used as a vital marker so that cell growth (for example, the elaboration of neuronal processes) and movement can be followed in situ, especially in animals that are essentially transparent like C. elegans and zebrafish. The relatively small size of the protein may facilitate its diffusion throughout the cytoplasm of extensively branched cells like neurons and glia. Since the GFP fluorescence persists after treatment with formaldehyde (9), fixed preparations can also be examined. In addition, absorption of appropriate laser light by GFP-expressing cells (as has been done for lucifer yellow-containing cells) (25), could result in the selective killing of the cells.

Further Experiments on GFP Expression

The TU#58 plasmid, which contains the green fluorescent protein (GFP) coding sequence in the pET3a expression vector (29) was transformed into Escherichia coli strain BLR (DE3) (A. Roca, University of Wisconsin: cited in the Novogen Catalogue) using procedures described previously (29). The resulting strain (SMC3), because of the reduced recombination of the host, was much more stable for GFP expression (all the colonies on plates with ampicillin but without the IPTG inducer (29) were brightly fluorescent when viewed with a hand-held UV lamp).

A second construct (TU#147), similar to TU#58, was made with pET11 (A. H. Rosenberg, et al. 1987). Expression in BLR (DE3) from this plasmid was more tightly controlled; expression was seen soon after IPTG was added, but only after some time without inducer.

The SMC3 strain was used to test the requirement for aerobic growth of the bacteria for the production of a fluorescent product. Plates were grown under anaerobic conditions in a Gas-Pak container according to the instructions of the manufacturer (Becton Dickinson Microbiology Systems). Colony growth was slowed under anaerobic conditions and the resulting colones were not detectably fluorescent after at least 3 days of growth under anaerobic conditions (using the hand-held UV lab). Colonies, however, became fluorescent after a day's exposure to room air (some fluorescence was seen after a few hours).

REFERENCES AND NOTES

1. O. Shimomura, F. H. Johnson, Y. Saiga, J. Cell. Comp. Physiol. 59, 223 (1962).

2. J. G. Morin and J. W. Hastings, J. Cell. Physiol. 77, 313 (1971); H. Morise, O. Shimomura, F. H. Johnson, J. Winant, Biochemistry 13, 2656 (1974).
3. D. C. Prasher, V. K. Eckenrode, W. W. Ward, F. G. Prendergast, M. J. Cormier, Gene 111, 229 (1992).
4. W. W. Ward, C. W. Cody, R. C. Hart, M. J. Cormier, Photochem. Photobiol. 31, 611 (1980).
5. F. G. Prendergast, personal communication.
6. O. Shimomura, FEBS Lett. 104, 220 (1979).
7. C. W. Cody, D. C. Prasher, W. M. Westler, F. G. Prendergast, W. W. Ward, Biochemistry 32, 1212 (1993).
8. Plasmid pGFP10.1 contains the EcoRI fragment encoding the GFP cDNA from λgfp10 (3) in pBS(+) (Stratagene®). The fragment was obtained by amplification with the polymerase chain reaction [PCR; R. K. Saiki et al., Science 239, 487 (1988)] with primers flanking the EcoRI sites and subsequent digestion with EcoRI. DNA was prepared by the Magic Minipreps procedure (Promega) and sequenced (after an additional ethanol precipitation) on an Applied Biosystems DNA Sequencer 370A at the DNA Sequencing facility at Columbia College of Physicians and Surgeons. The sequence of the cDNA in pGFP10.1 differs from the published sequence by a change in codon 80 within the coding sequence from CAG to CGG, a change that replaces a glutamine residue with arginine [R. Heim, S. Emr, and R. Tsien (personal communication) first alerted us to a possible sequence change in this clone and independently noted the same change.] This replacement has no detectable effect on the spectral properties of the protein (FIG. 2).

An E. coli expression construct was made with PCR to generate a fragment with an NheI site at the start of translation and an EcoRI site 5' to the termination signal of the GFP coding sequence from PGFP10.1 . The 5' primer was ACAAAGGCTAGCAAAGGAGAAGAAC (Sequence ID No. 1) and the 3' primer was the T3 primer (Stratagene®). The NheI-EcoRI fragment was ligated into the similarly cut vector pET3a [A. H. Rosenberg et al., Gene 56, 125 (1987)] by standard methods (26). The resulting coding sequence substitutes an Ala for the initial GFP Met, which becomes the second amino acid in the polypeptide. The E. coli strain BL21(DE3)Lys S [F. W. Studier and B. A. Moffat, J. Mol. Biol. 189, 113 (1986)] was transformed with the resulting plasmid (TU#58) and grown at 37° C. Control bacteria were transformed with pET3a. Bacteria were grown on nutrient plates containing ampicillin (100 μg/ml) and 0.8 mM IPTG. Transformed bacteria from this transformation show green fluorescence when irradiated with ultraviolet light. A recombinant plasmid of this bacteria was used for the experiments described here and the experiment in FIG. 2 and the experiment in Note 10. Several months later, applicants noticed that the bacterial colonies can be divided into two groups: 1) strongly fluorescent; and 2) weakly fluorescent (applicants believe that the weakly fluorescent may have mutated, disabled or partial or completely deleted TU#58). One strongly fluorescent colony was picked to generate the bacterial strain SMC1 (ATCC Accession No. 69554). [A similar PCR-generated fragment (see note 11) was used in applicants' C. elegans construct. As others are beginning to use pGFP10.1, applicants have heard that while similar PCR fragments produce a fluorescent product in other organisms (R. Heim, S. Emr, and R. Tsien, personal communication; S. Wang and T. Hazelrigg, personal communication; L. Lanini and F. McKeon, personal communication; see note 23), the EcoRI fragment does not (R. Heim, S. Emr, and R. Tsien, personal communication; A. Coxon, J. R. Chaillet, and T. Bestor, personal communication). These results may indicate that elements at the 5' end of the sequence or at the start of translation inhibit expression.]

9. Applicants used a variety of microscopes (Zeiss Axiophot, Nikon Microphot FXA, and Olympus BH2-RFC and BX50) equipped for epifluorescence microscopy. Usually filter sets for fluorescein isothiocyanate fluorescence were used (for example, the Zeiss filter set used a BP450–490 excitation filter, 510 nm dichroic, and either a BP515–565 or a LP520 emission filter), although for some experiments filter sets that excited at lower wavelengths were used (for example, a Zeiss filter set with BP395–440 and LP470 filters and a 460 nm dichroic or with BP340–390 and LP400 filters with a 395 nm dichroic). In some instances a xenon lamp appeared to give a more intense fluorescence than a mercury lamp when cells were illuminated with light around 470 nm, although usually the results were comparable. No other attempts were made to enhance the signal (for example, by using low intensity light cameras), although this may be useful in some instances.

Previous experiments had shown that the native protein was fluorescent after glutaraldehyde fixation (W. W. Ward, unpub. data). S. Wang and T. Hazelrigg (personal communication; 23) have found that GFP fusion proteins in *Drosophila melanogaster* are fluorescent after formaldehyde fixation. Applicants have confirmed that fluorescence persists after formaldehyde fixation with applicants' *C. elegans* animals and with recombinant GFP isolated from *E. coli*. The chemicals in nail polish, which is often used to seal cover slips, however, did appear to interfere with the *C. elegans* GFP fluorescence.

10. In the applicants' initial experiments, GFP was purified from 250 ml cultures of BL21(DE3)Lys S bacteria containing TU#58; bacteria were grown in LB broth (26) containing ampicillin (100 $\mu$g/ml) and 0.8 mM IPTG. Induction was best when IPTG was present continually. Nevertheless, subsequent experiments with bacterial strain SMC1 indicate that the bacteria could not grow in the constant presence of IPTG but can be induced by the IPTG during the log phase growth. The production of fluorescent protein is best at room temperature. Cells were washed in 4 ml of 10 mM Tris-HCl (pH 7.4), 100 mM NaCl, 1 mM $MgCl_2$, and 10 mM dithiothreitol [A. Kumagai and W. G. Dunphy, *Cell* 64, 903 (1991)] and then sonicated (2×20 sec) in 4 ml of the same buffer containing 0.1 mM PMSF, pepstatin A (1 $\mu$g/ml), leupeptin (1 $\mu$g/ml), and aprotinin (2 $\mu$g/ml), and centrifuged at 5,000 rpm for 5 min in the cold. The supernatant was centrifuged a second time (15,000 rpm for 15 min) and then diluted sevenfold with 10 mM Tris (pH 8.0), 10 mM EDTA, and 0.02% $NaN_3$. Corrected excitation and emission spectra were obtained with a SPEX FIT11 spectrofluorometer and compared with the purified L isoprotein form of GFP from *A. victoria* (M. Cutler, A. Roth, and W. W. Ward, unpub. data). The excitation spectra were measured from 300–500 nm with a fixed emission wavelength of 509 nm, and the emission spectra were measured from 410–600 nm with a fixed excitation of 395 nm. All spectra were recorded as signal-reference data (where the reference is a direct measurement of the lamp intensity with a separate photomultiplier tube) at room temperature with 1 sec integration times and 1 nm increments. The spectral band widths were adjusted to 0.94 nm for all spectra.

11. Wild-type and mutant C. elegans animals were grown and genetic strains were constructed according to S. Brenner, *Genetics* 77, 71 (1974).

The plasmid pGFP10.1 was used as a template for PCR (with the 5' primer GAATAAAAGCTAGCAAAGATGAG-TAAAG (Sequence ID No. 2) and the 3' T3 primer) to generate a fragment with a 5' NheI site (at the start of translation) and a 3' EcoRI site (3' of the termination codon). The DNA was cut to produce an NheI—EcoRI fragment that was ligated into plasmid pPD 16.51 (12, 27), a vector containing the promoter of the *C. elegans* mec-7 gene. Wild-type *C. elegans* were transformed by coinjecting this DNA (TU#64) and the DNA for plasmid pRF4, which contains the dominant rol-6(sul006) mutation, into adult C. elegans gonads as described by C. M. Mello, J. M. Kramer, D. Stinchcomb, and V. Ambros, *EMBO J.* 10, 3959 (1991). A relatively stable line was isolated (TU1710) and the DNA it carried was integrated as described by Mitani et al. (15) to produce the integrated elements uIs3 and uIs4 (in strains TU1754 and TU1755, respectively).

Living *C. elegans* animals were mounted on agar (or agarose) pads as described (16), often with 10 mM $NaN_3$ as an anesthetic (28) (another nematode anesthetic, phenoxypropanol, quenched the fluorescence) and examined with either a Zeiss universal or axiophot microscope. For *C. elegans*, a long-pass emission filter works best because the animal's intestinal autofluorescence, (which increases as the animal matures), appears yellow (with band-pass filters the autofluorescence appears green and obscures the GFP fluorescence).

Because much more intense fluorescence was seen in uIs4 than uIs3 animals (for example, it was often difficult to see the processes of the ALM and PLM cells in uIs3 animals when the animals were illuminated with a mercury lamp), the former have been used for the observations reported here. The general pattern of cell body fluorescence was the same in both strains and in the parental, nonintegrated strain (fluorescence in this strain was as strong as that in the uIs4 animals). The uIs4 animals, however, did show an unusual phenotype: both the ALM and PLM touch cells were often displaced anteriorly. The mature cells usually had processes in the correct positions, although occasional cells had abnormally-projecting processes. These cells could be identified as touch receptor cells, because the fluorescence was dependent on mec-3, a homeobox gene that specifies touch cell fate (13, 15, 18, 28). mec-7 expression is reduced in the ALM touch cells of the head (but not as dramatically in the PLM touch cells of the tail) in mec-3 gene mutants (13, 15). Applicants find a similar change of GFP expression in a mec-3 mutant background for both uIs3 and uIs4. Thus, GFP accurately represents the expression pattern of the mec-7 gene. It is likely that the reduced staining in uIs3 animals and the misplaced cells in uIs4 animals is the result of either secondary mutations or the amount and position of the integrated DNA.

12. C. Savage, M. Hamelin, J. G. Culotti, A. Coulson, D. G. Albertson, M. Chalfie, Genes Dev. 3, 870 (1989).
13. M. Hamelin, I. M. Scott, J. C. Way, J. G. Culotti, *EMBO J.* 11, 2885 (1992).
14. A. Duggan and M. Chalfie, unpub. data.
15. S. Mitani, H. P. Du, D. H. Hall, M. Driscoll, M. Chalfie, *Development* 119, 773 (1993).
16. J. E. Sulston and H. R. Horvitz, *Develop. Biol.* 56, 110 (1977).

17. W. W. Walthall and M. Chalfie, Science 239, 643 (1988).
18. M. Chalfie and J. Sulston, *Dev. Biol.* 82, 358 (1981).
19. In adults, the thicker size of the animals and the more intense autofluorescence of the intestine tend to obscure these cells.
20. These include several cells in the head (including the FLP cells) and tail of newly hatched animals and the BDU cells, a pair of neurons just posterior to the pharynx. Expression of mec-7 in these cells has been seen previously (13, 15). The strongest staining of these non-touch receptor neurons are a pair of cells in the tail that have anteriorly directed processes that project along the dorsal muscle line. It is likely that these are the ALN cells, the sister cells to the PLM touch cells [J. G. White, E. Southgate, J. N. Thomson, and S. Brenner, *Philos. Trans. R. Soc. Lond. B Biol. Sci.* 314, 1 (1986).]
21. The photobleaching with 395–440 nm light is further accelerated, to within seconds, in the presence of 10 mM $NaN_3$, which is used as a *C. elegans* anesthetic (11). However, when cells in *C. elegans* have been photobleached, some recovery is seen within 10 min. Further investigation is needed to determine whether this recovery represents de novo synthesis of GFP. Rapid photobleaching (complete within a minute) of the green product was also seen when *C. elegans* was illuminated with 340–390 nm light. Unlike the photobleaching with 395–440 nm light, which abolished fluorescence produced by the 340–390 or 450–490 nm light, photobleaching with 340–390 nm light did not appear to affect the fluorescence produced by 395–490 or 450–490 nm light. Indeed, the fluorescence produced by 450–490 nm light appeared to be more intense after brief photobleaching by 340–390 nm light. This selective photobleaching may indicate the production of more than one fluorescent product in the animal. These data on GFP fluorescence within *E. coli* and *C. elegans* is in contrast to preliminary studies that suggest that the isolated native and *E. coli* proteins are very photostable. Applicants do not know whether this in vivo sensitivity to photobleaching is a normal feature of the jellyfish protein (the fluorescence in *A. victoria* has not been examined) or results from the absence of a necessary posttranslational modification unique to *A. victoria* or nonspecific damage within the cells.
22. Reviewed in T. J. Silhavy and J. R. Beckwith, *Microbiol. Rev.* 49, 398 (1985); S. J. Gould and S. Subramani, *Anal. Biochem.* 175, 5 (1988); and G. S. A. B. Stewart and P. Williams, *J. Gen. Microbiol.* 138, 1289 (1992).
23. R. Heim, S. Emr, and R. Tsien (personal communication) have found that GFP expression in *Saccharomyces cerevisiae* can make the cells strongly fluorescent without causing toxicity. S. Wang and T. Hazelrigg (personal communication) have found that both C-terminal and N-terminal protein fusions with GFP are fluorescent in *Drosophila melanogaster*. L. Lanini and F. McKeon (personal communication) have expressed a GFP protein fusion in mammalian (COS) cells. E. Macagno (personal communication) is expressing GFP in leeches. T. Hughes (personal communication) is expressing GFP in mammalian HEK293 cells.
24. Applicants have generated several other plasmid constructions that may be useful to investigators. These include a pBluescript II KS (+) derivative (TU#65) containing a KpnI—EcoRI fragment encoding GFP with an AgeI site 5' to the translation start and a BsmI site at the termination codon. Also available are gfp versions (TU#60–TU#63) of the four *C. elegans* lacZ expression vectors (pPD16.43, pPD21.28, pPD22.04, and pPD22.11, respectively) described by Fire et al., 1990 (27) except that they lack the KpnI fragment containing the SV40 nuclear localization signal.
25. J. P. Miller and A. Selverston, *Science* 206, 702 (1979).
26. J. Sambrook, E. F. Fritsch, and T. Maniatis, *Molecular cloning: A laboratory manual,* 2nd Ed. Cold Spring Harbor Laboratory Press, Cold Spring Harbor, New York, (1989).
27. A. Fire, S. W. Harrison, and D. Dixon, *Gene* 93, 189 (1990).
28. J. C. Way and M. Chalfie, *Cell* 54, 5 (1988).
29. Chalfie, M., Tu. Y., Euskirchen, G., Ward, W. W., Prasher, D. C., *Science* 263, 802 (1994).

What is claimed is:

1. A cell comprising a DNA molecule having a regulatory element from a gene, other than a gene encoding a green fluorescent protein, operatively linked to a DNA sequence encoding a fluorescent mutant of green fluorescent protein of *Aequorea victoria*.

2. The cell of claim 1, wherein the cell is selected from the group consisting of a bacterial cell, a yeast cell, a fungal cell, a plant cell and an animal cell.

3. The cell of claim 1, wherein the regulatory element is a promoter.

4. The cell of claim 1, wherein the regulatory element is an enhancer.

5. The cell of claim 1, wherein the cell is an *E. coli* cell.

6. A method to produce a fluorescent mutant of green fluorescent protein of *Aequorea victoria* comprising:
   a) culturing the cell of claim 1 so that the cell produces the fluorescent mutant; and
   b) isolating and purifying the fluorescent mutant so produced by the cell.

7. The cell of claim 1, wherein the cell is an insect cell or a nematode cell.

8. The cell of claim 3, wherein the promoter is activated by a heavy metal.

9. The cell of claim 3, wherein the promoter is that from a P450 gene.

10. The cell of claim 3, wherein the promoter is from a gene encoding a stress protein.

11. The cell of claim 3, wherein the promoter is from a gene required for cell viability.

12. The cell of claim 5 designated pGFP10.1 (ATCC Accession No. 75547).

13. The method of claim 6, wherein the cell is an *E. coli* cell.

14. The cell of claim 10, wherein the stress protein is a heat-shock protein.

15. The method of claim 13, wherein the cell is cultured aerobically.

16. A method for selecting cells expressing a protein of interest which comprises:
   a) introducing into the cells a first DNA molecule having a DNA sequence encoding the protein of interest and a second DNA molecule having a DNA sequence encoding a fluorescent mutant of green fluorescent protein of *Aeguorea victoria*;
   b) culturing cells resulting from step (a) under conditions permitting expression of the fluorescent mutant of green fluorescent protein and the protein of interest; and
   c) selecting the cultured cells which express the fluorescent mutant of green fluorescent protein, thereby selecting cells expressing the protein of interest.

17. The method of claim 16, wherein the first DNA molecule and the second DNA molecule are linked.

18. The method of claim 16, wherein the cells are selected from the group consisting of bacterial cells, yeast cells, fungal cells, plant cells and animal cells.

19. The method of claim 16, wherein the cells are insect cells or nematode cells.

20. A method for localizing a protein of interest in a cell which comprises:
   a) introducing into a cell a DNA molecule having a sequence encoding the protein of interest linked to a DNA sequence encoding a fluorescent mutant of green fluorescent protein of *Aequorea victoria* such that the protein produced by the DNA molecule will have the protein of interest fused to the fluorescent mutant of green fluorescent protein of *Aequorea victoria*;
   b) culturing the cell under conditions permitting expression of the fused protein; and
   c) detecting the location of the fused protein, thereby localizing the protein of interest in the cell.

21. The method of claim 20, wherein the cell normally expresses the protein of interest.

22. A method of detecting expression of a gene in a cell which comprises:
   a) introducing into the cell a DNA molecule having the sequence of the gene linked to a DNA molecule encoding a fluorescent mutant of green fluorescent protein of *Aequorea victoria* such that a regulatory element of the gene controls expression of the fluorescent mutant of green fluorescent protein of *Aequorea victoria*;
   b) culturing the cell under conditions permitting expression of the gene; and
   c) detecting the expression of the fluorescent mutant of green fluorescent protein of *Aequorea victoria* in the cell, thereby detecting expression of the gene in the cell.

23. A method for detecting expression of a gene in a living organism which comprises:
  a) introducing into a cell of the subject a DNA molecule having the sequence of the gene linked to a DNA molecule encoding a fluorescent mutant of green fluorescent protein of *Aequorea victoria* such that a regulatory element of the gene controls expression of the fluorescent mutant of green fluorescent protein of *Aequorea victoria*;
  b) culturing the cell under conditions permitting expression of the gene; and
  c) detecting the expression of the fluorescent mutant of green fluorescent protein of *Aequorea victoria* in the cell, thereby detecting expression of the gene in the living organism.

24. A method for determining the tissue-specificity of transcription of a first DNA sequence in a living organism which comprises:
  a) introducing into a cell of the living organism a DNA molecule which comprises the first DNA sequence linked to a second DNA sequence encoding a fluorescent mutant of green fluorescent protein of *Aequorea victoria* such that the first DNA sequence controls expression of the fluorescent mutant of green fluorescent protein of *Aequorea victoria* in the living organism; and detecting expression of the fluorescent mutant of green fluorescent protein of *Aequorea victoria* in different tissues of the living organism, thereby determining the tissue-specificity of the transcription of the first DNA sequence in the living organism.

25. A method for producing a fluorescent molecular weight protein marker comprising:
  a) linking a first DNA molecule encoding a fluorescent mutant of green fluorescent protein of *Aequorea victoria* with a second DNA molecule encoding a known amino acid sequence which is in the same reading frame as the first DNA molecule;
  b) introducing the linked DNA molecule of step (a) into a protein expression system permitting the expression of a fusion protein comprising the fluorescent mutant linked to the known amino acid sequence;
  c) recovering the fusion protein expressed in step (b): and
  d) determining the molecular weight of the fusion protein from step (c), thereby producing a fluorescent molecular weight protein marker.

26. The method of claim 25, further comprising purification of the expressed protein.

\* \* \* \* \*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (vi) ORIGINAL SOURCE:
    (A) ORGANISM: Escherichia coli (xi) SEQUENCE DESCRIPTION: SEQ ID NO:1:

```
ACAAAGGCTA GCAAAGGAGA AGAAC                                              25

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Escherichia coli (xi) SEQUENCE DESCRIPTION: SEQ ID NO:2:

GAATAAAAGC TAGCAAAGAT GAGTAAAG                                           28
```